(12) United States Patent
Takenaka et al.

(10) Patent No.: US 11,802,846 B2
(45) Date of Patent: Oct. 31, 2023

(54) OXYGEN CONCENTRATION METER, OXYGEN CONCENTRATION DETECTION SYSTEM, AND METHOD OF DETECTING RESISTANCE OF ZIRCONIA SENSOR

(71) Applicant: YOKOGAWA ELECTRIC CORPORATION, Tokyo (JP)

(72) Inventors: Kouichi Takenaka, Tokyo (JP); Ken Ito, Tokyo (JP)

(73) Assignee: YOKOGAWA ELECTRIC CORPORATION, Tokyo (JP)

(*) Notice: Subject to any disclaimer, the term of this patent is extended or adjusted under 35 U.S.C. 154(b) by 0 days.

(21) Appl. No.: 17/680,566

(22) Filed: Feb. 25, 2022

(65) Prior Publication Data

US 2022/0283108 A1 Sep. 8, 2022

(30) Foreign Application Priority Data

Mar. 5, 2021 (JP) ................................. 2021-035787

(51) Int. Cl.
*G01N 27/12* (2006.01)
*G01N 33/00* (2006.01)
*F02D 41/10* (2006.01)

(52) U.S. Cl.
CPC ......... *G01N 27/12* (2013.01); *G01N 33/0036* (2013.01)

(58) Field of Classification Search
CPC ............ F02D 41/1494; F02D 41/1441; G01N 27/409
See application file for complete search history.

(56) References Cited

U.S. PATENT DOCUMENTS

| 4,027,477 A | * | 6/1977 | Storey | ................. F02D 41/1441 60/276 |
| 5,632,883 A | | 5/1997 | Hoetzel | |
| 5,928,494 A | | 7/1999 | Kato et al. | |

(Continued)

FOREIGN PATENT DOCUMENTS

| JP | 4-13961 A | 1/1992 |
| JP | 6-27078 A | 2/1994 |
| JP | 2006-17695 A | 1/2006 |

OTHER PUBLICATIONS

Extended European Search Report (EESR) dated Jul. 11, 2022 for European Patent Application No. 22158869.2.

*Primary Examiner* — Jermele M Hollington
*Assistant Examiner* — Temilade S Rhodes-Vivour
(74) *Attorney, Agent, or Firm* — Rankin, Hill & Clark LLP (57) ABSTRACT

An oxygen concentration meter includes a zirconia sensor, a resistor, a constant-current circuit, a resistance detection section, and an oxygen concentration detection section. The resistor is connected in parallel to the zirconia sensor. The constant-current circuit is connected in parallel to the zirconia sensor and the resistor, and supplies an electric current. The resistance detection section detects the resistance of the zirconia sensor on the basis of the voltage of the zirconia sensor in accordance with the supplied electric current. The oxygen concentration detection section detects the oxygen concentration of gas to be measured that is supplied to the zirconia sensor, on the basis of the voltage of the zirconia sensor resulting from an oxygen concentration difference between the gas to be measured and reference gas.

8 Claims, 6 Drawing Sheets

(56) References Cited

U.S. PATENT DOCUMENTS

| | | | | |
|---|---|---|---|---|
| 5,980,728 A | * | 11/1999 | Farber | G01N 27/4175 |
| | | | | 205/784.5 |
| 2004/0195097 A1 | * | 10/2004 | Suzuki | G01N 27/4071 |
| | | | | 204/426 |
| 2005/0263396 A1 | * | 12/2005 | Naito | G01N 27/4072 |
| | | | | 29/592.1 |
| 2005/0263408 A1 | | 12/2005 | Hazama et al. | |
| 2006/0290525 A1 | * | 12/2006 | Andersen | G16H 40/20 |
| | | | | 340/632 |
| 2011/0197657 A1 | * | 8/2011 | Gole | G01N 27/127 |
| | | | | 438/49 |
| 2018/0209873 A1 | * | 7/2018 | Monna | F01N 11/00 |

\* cited by examiner

OXYGEN CONCENTRATION METER, OXYGEN CONCENTRATION DETECTION SYSTEM, AND METHOD OF DETECTING RESISTANCE OF ZIRCONIA SENSOR

CROSS-REFERENCE TO RELATED APPLICATION(S)

The present application claims priority to and incorporates by reference the entire contents of Japanese Patent Application No. 2021-035787 filed in Japan on Mar. 5, 2021.

FIELD

The present disclosure relates to an oxygen concentration meter, an oxygen concentration detection system, and a method of detecting the resistance of a zirconia sensor.

BACKGROUND

Oxygen concentration meters have been used that include stabilized zirconia in which the crystal structure is made stable by adding a stabilizer to zirconium oxide (zirconia). Such stabilized zirconia generates electromotive force in accordance with an oxygen concentration difference. Specifically, introducing gases having different oxygen concentrations to one face and the other face of a partition formed of stabilized zirconia generates electromotive force in accordance with an oxygen concentration difference at a partition formed of stabilized zirconia under high temperature conditions. The oxygen concentration of gas to be measured can be measured by using a zirconia sensor based on such stabilized zirconia to detect an oxygen concentration difference between gas (reference gas) having a known oxygen concentration and the gas to be measured.

In such a zirconia sensor, sensor outputs vary with age. For this reason, an oxygen concentration meter that uses a zirconia sensor needs the sensor outputs to be calibrated as appropriate. The calibration can be performed by using standard gases, which are gases each having a predetermined oxygen concentration. For the standard gases, a zero gas, which is a standard gas containing 1% oxygen and 99% nitrogen, and a span gas, which is a standard gas containing 21% oxygen and 79% nitrogen, can be used. Specifically, span calibration can be performed with an oxygen concentration output obtained when the span gas is introduced to both faces of a partition of the zirconia sensor, and zero-point calibration can be performed with an oxygen concentration output when the span gas and the zero gas are introduced to different faces of the partition of the zirconia sensor. Calibration methods have been proposed for determining the next calibration date on the basis of the calibration history (see Japanese Patent Application Laid-open No. 2006-017695, for example).

With the above-mentioned age, the zirconia sensor undergoes deterioration of the performance, such as electromotive force and response time. It has been known that a rise in internal resistance of the zirconia sensor shows the deterioration. The initial internal resistance of the zirconia sensor is equal to or smaller than 200Ω. Contrarily, the internal resistance of the zirconia sensor that has undergone a change over time rises to a few kΩ. The internal resistance can be calculated based on the open terminal voltage of the zirconia sensor and the terminal voltage when terminated with a known resistor in a state in which electromotive force is generated by introducing the span gas and the zero gas to the zirconia sensor. The internal resistance can be measured during the above-mentioned calibration, for example.

SUMMARY OF THE INVENTION

The above-mentioned resistance measurement has the problem of needing the span gas and the zero gas that is relatively expensive, which decreases convenience.

Therefore, the present disclosure proposes an oxygen concentration meter, an oxygen concentration detection system, and a method of detecting the resistance of a zirconia sensor that increase convenience of resistance measurement.

According to one aspect of embodiments, an oxygen concentration meter comprising a zirconia sensor; a resistor connected in parallel to the zirconia sensor; a constant-current circuit that is connected in parallel to the zirconia sensor and the resistor, and that supplies an electric current; a resistance detection section configured to detect a resistance of the zirconia sensor, based on a voltage of the zirconia sensor in accordance with the supplied electric current; and an oxygen concentration detection section configured to detect an oxygen concentration of gas to be measured that is supplied to the zirconia sensor, based on the voltage of the zirconia sensor resulting from an oxygen concentration difference between the gas to be measured and reference gas.

According to one aspect of embodiments, an oxygen concentration detection system comprising; a zirconia sensor; a resistor connected in parallel to the zirconia sensor; a constant-current circuit that is connected in parallel to the zirconia sensor and the resistor, and that supplies an electric current; a resistance detection section configured to detect a resistance of the zirconia sensor, based on a voltage of the zirconia sensor in accordance with the supplied electric current; an oxygen concentration detection section configured to detect an oxygen concentration of gas to be measured that is supplied to the zirconia sensor, based on the voltage of the zirconia sensor resulting from an oxygen concentration difference between the gas to be measured and reference gas; and a deterioration detection section configured to detect an abnormality in the zirconia sensor, based on the detected resistance of the zirconia sensor.

According to one aspect of embodiments, a method of detecting a resistance of a zirconia sensor, the method comprising detecting a resistance of a zirconia sensor, based on a voltage of the zirconia sensor when a resistor is connected in parallel to the zirconia sensor and a voltage of the zirconia sensor when a constant-current circuit is connected in parallel to the zirconia sensor and the resistor and an electric current is supplied.

DETAILED DESCRIPTION OF THE PREFERRED EMBODIMENTS

Embodiments of the present disclosure are described in detail below with reference to the drawings. In the following embodiments, the same reference signs are given to the same sections, and overlapping descriptions are thus omitted.

Configuration of Oxygen Concentration Detection System

Figure 1:
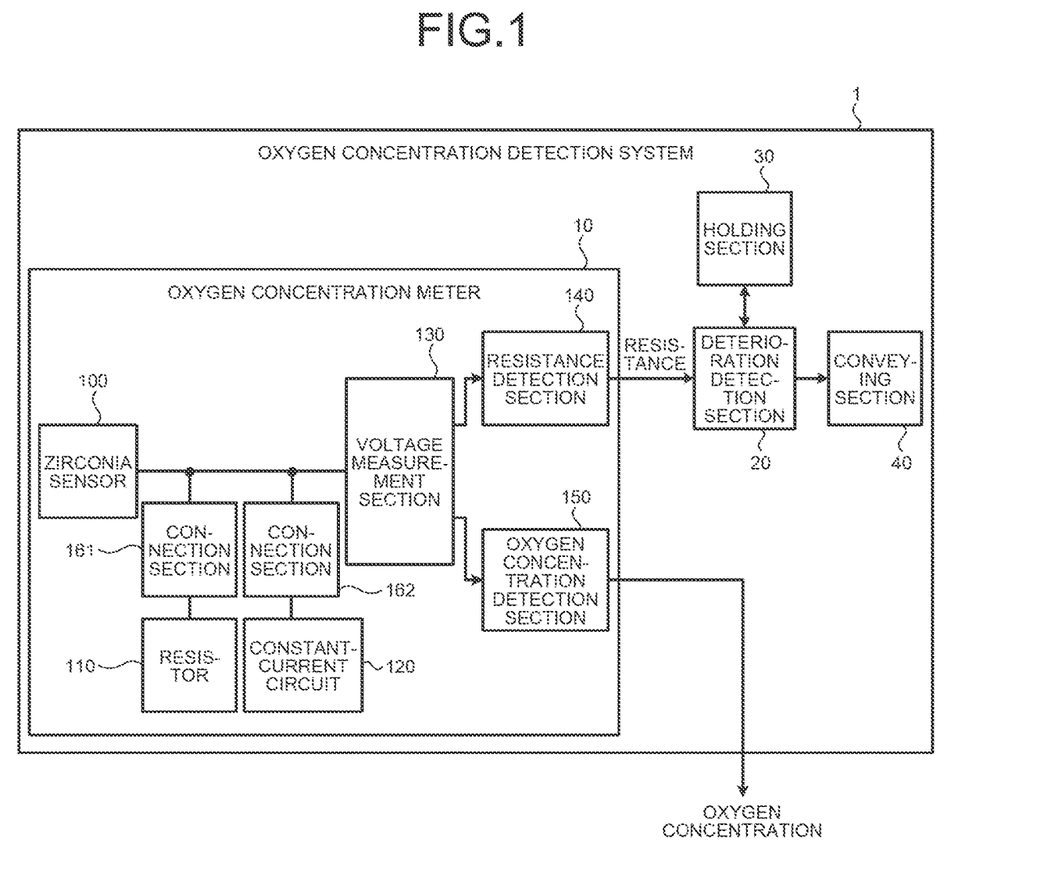
FIG. 1 is a diagram illustrating a configuration example of an oxygen concentration detection system according to an embodiment.

FIG. 1 is a diagram illustrating a configuration example of an oxygen concentration detection system according to an embodiment. FIG. 1 is a block diagram illustrating a configuration example of an oxygen concentration detection system 1. The oxygen concentration detection system 1 includes an oxygen concentration meter 10, a deterioration detection section 20, a holding section 30, and a conveying section 40.

The oxygen concentration meter 10 includes a zirconia sensor (a zirconia sensor 100 in FIG. 1) and measures the oxygen concentration of gas to be measured. The oxygen concentration meter 10 measures and outputs the oxygen concentration of the gas to be measured by detecting an oxygen concentration difference between reference gas having a known oxygen concentration and the gas to be measured. The oxygen concentration meter 10 further measures the resistance of the zirconia sensor 100. With a change in the resistance, an abnormality in the zirconia sensor 100 can be detected. Herein, an abnormality in the zirconia sensor 100 represents deterioration and breakage with aging of the zirconia sensor 100. The oxygen concentration meter 10 further outputs the measured resistance of the zirconia sensor 100.

The deterioration detection section 20 detects an abnormality in the zirconia sensor 100. The deterioration detection section 20 detects deterioration of the zirconia sensor 100 on the basis of the resistance of the zirconia sensor 100 that has been output from the oxygen concentration meter 10. For example, when the resistance of the zirconia sensor 100 reaches a predetermined threshold, the deterioration detection section 20 can determine that the zirconia sensor 100 has deteriorated. The deterioration detection section 20 also causes the holding section 30 to hold the resistance (resistance value) of the zirconia sensor 100 that has been output from the oxygen concentration meter 10. The deterioration detection section 20 can detect a change in resistance on the basis of the resistance held by the holding section 30, and detect aging of the zirconia sensor 100. The deterioration detection section 20 can also analyze the progress of deterioration from the aging, and predict deterioration. The deterioration detection section 20 can also detect breakage of the zirconia sensor 100. Specifically, when the resistance value of the zirconia sensor 100 changes quickly, the deterioration detection section 20 can detect breakage of the zirconia sensor 100.

The holding section 30 holds the resistance of the zirconia sensor 100. The holding section 30 can be composed of a storage device, such as a hard disk, for example. The holding section 30 holds the resistance of the zirconia sensor 100 chronologically under control from the deterioration detection section 20. For example, the deterioration detection section 20 can hold (store) the resistance value of the zirconia sensor 100 in correspondence with detection time.

The conveying section 40 conveys the abnormality in the zirconia sensor 100 that has been detected by the deterioration detection section 20. For example, the conveying section 40 can be composed of a display device. Analytical results of the abnormality in the zirconia sensor 100 can be conveyed to a user by displaying the results on the display device. For example, a device that issues an alarm to a host system can also be applied to the conveying section 40.

Configuration of Oxygen Concentration Meter

The oxygen concentration meter 10 in FIG. 1 includes the zirconia sensor 100, a resistor 110, a constant-current circuit 120, a voltage measurement section 130, a resistance detection section 140, and an oxygen concentration detection section 150. The oxygen concentration meter 10 in FIG. 1 further includes connection sections 161 and 162.

The zirconia sensor 100 is a sensor device that is composed of stabilized zirconia and that detects an oxygen concentration. The zirconia sensor 100 is configured as a two-terminal device, and outputs voltage in accordance with an oxygen concentration difference between gas to be measured and reference gas. The details of the configuration of the zirconia sensor 100 will be described later.

The resistor 110 is a resistor that is connected in parallel to the zirconia sensor 100 when the resistance of the zirconia sensor 100 is measured.

The constant-current circuit 120 is a circuit that is connected in parallel to the zirconia sensor 100 and supplies a constant current when the resistance of the zirconia sensor 100 is measured. A known circuit can be applied to the constant-current circuit 120.

The connection section 161 connects the resistor 110 to the zirconia sensor 100 when the resistance of the zirconia sensor 100 is measured. The connection section 162 connects the constant-current circuit 120 to the zirconia sensor 100 when the resistance of the zirconia sensor 100 is measured. A switch, which will be described later, can be used for these connection sections 161 and 162.

The voltage measurement section 130 measures the terminal voltage of the zirconia sensor 100. The voltage measurement section 130 includes a voltmeter (voltmeter 131, which will be described later). The voltage measurement section 130 measures the terminal voltage of the zirconia sensor 100 by means of the voltmeter 131. The measured voltage of the zirconia sensor 100 is output to the resistance detection section 140 and the oxygen concentration detection section 150.

The resistance detection section 140 detects the resistance of the zirconia sensor 100. The resistance detection section 140 detects the resistance of the zirconia sensor 100 on the basis of the voltage of the zirconia sensor 100 that has been output from the voltage measurement section 130. The details of the resistance detection section 140 detecting the resistance of the zirconia sensor 100 will be described later.

The oxygen concentration detection section 150 detects an oxygen concentration. The oxygen concentration detection section 150 detects the oxygen concentration of the gas to be measured, on the basis of the voltage of the zirconia sensor 100 that has been output from the voltage measurement section 130. The details of the oxygen concentration detection section 150 detecting the oxygen concentration will be described later.

Configuration of Zirconia Sensor

Figure 2:
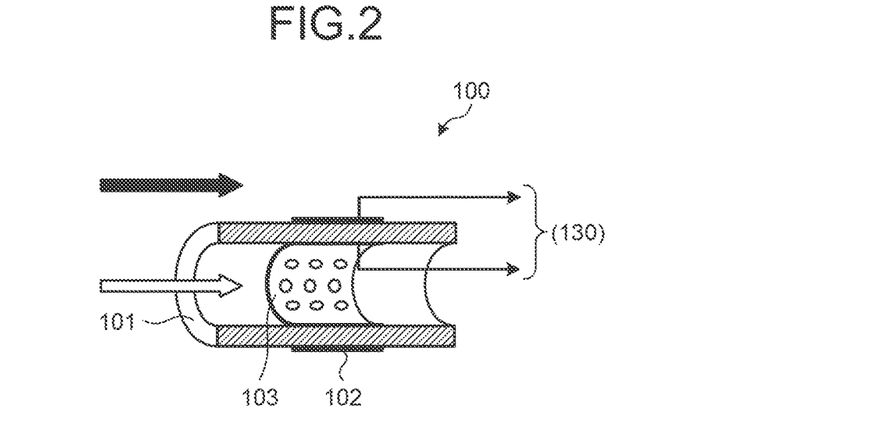
FIG. 2 is a diagram illustrating a configuration example of a zirconia sensor according to the embodiment.

FIG. 2 is a diagram illustrating a configuration example of the zirconia sensor according to the embodiment. FIG. 2 is a sectional diagram schematically illustrating the configuration of the zirconia sensor 100. The zirconia sensor 100 includes a zirconia tube 101 and electrodes 102 and 103.

The zirconia tube 101 is goods processed by making stabilized zirconia into a tube. The zirconia tube 101 generates electromotive force in accordance with an oxygen concentration difference between gases introduced to the inside and the outside of the zirconia tube 101. The zirconia tube 101 corresponds to the above-mentioned partition.

The electrodes 102 and 103 are placed in the zirconia tube 101. The electrode 102 is placed outside the zirconia tube 101, and the electrode 103 is placed inside the zirconia tube 101. The electrodes 102 and 103 can be composed of porous platinum. The electrodes 102 and 103 can take the electromotive force of the zirconia tube 101 to the exterior. The electrodes 102 and 103 are both connected to two output terminals of the zirconia sensor 100.

The zirconia tube 101 is heated to 750° C. by a heater not illustrated. The high-temperature zirconia tube 101 becomes a solid electrolyte and acts as an oxygen concentration cell. FIG. 2 illustrates an example of a case where the gas to be measured is passed through the inside of the zirconia tube 101 and the reference gas is passed through the outside of the zirconia tube 101. A gas having a known oxygen concentration, such as the air, can be used for the reference gas. A white arrow in FIG. 2 indicates the flow of the gas to be measured, and a black arrow indicates the flow of the reference gas. The zirconia tube 101 generates electromotive force in accordance with an oxygen concentration difference between these gases in the thickness direction. By the electrodes 102 and 103 taking out the voltage of the electromotive force, the voltage in accordance with the oxygen concentration difference can be output.

Measurement of Resistance of Zirconia Sensor

Figure 3A:
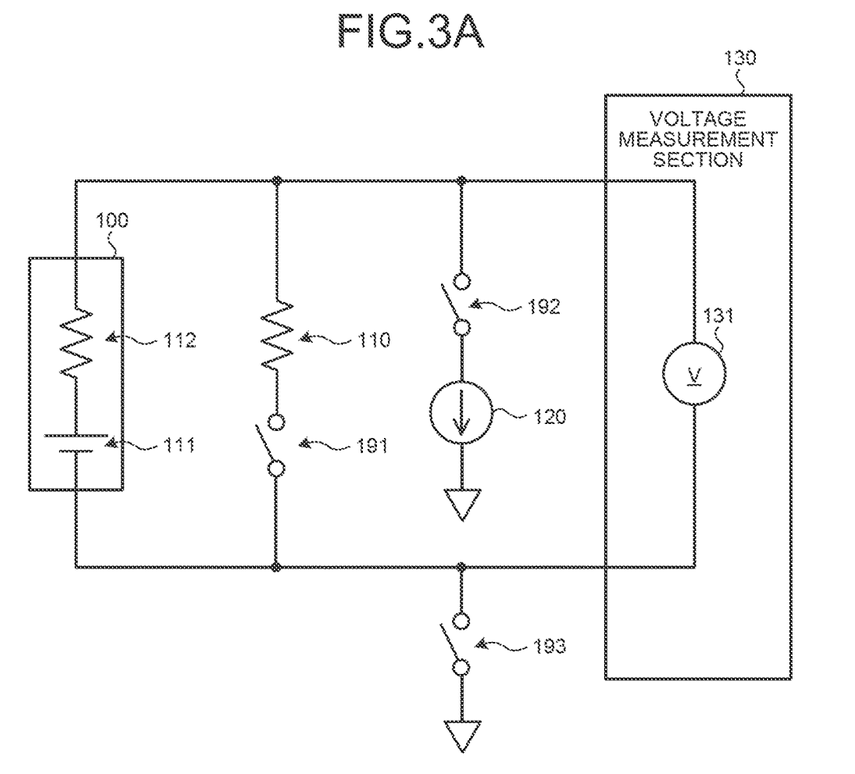
FIG. 3A is a diagram illustrating an example of measuring the resistance of the zirconia sensor according to the embodiment.

FIG. 3A is a diagram illustrating an example of measuring the resistance of the zirconia sensor according to the embodiment. FIG. 3A is a diagram illustrating connection of a circuit when the resistance of the zirconia sensor 100 is measured. Measurement of the resistance of the zirconia sensor 100 is described with reference to FIG. 3A. The circuit in FIG. 3A includes the zirconia sensor 100, the resistor 110, the constant-current circuit 120, switches 191 to 193, and the voltmeter 131. The voltmeter 131 is included in the voltage measurement section 130.

As illustrated in FIG. 3A, the zirconia sensor 100 can be represented by a voltage source 111 and a resistor 112 connected in series. The voltage source 111 is a voltage source of the voltage corresponding to the electromotive force in accordance with the oxygen concentration difference. The resistor 112 is the internal resistance of the zirconia sensor 100. The circuit in FIG. 3A measures the resistance value of the resistor 112. For convenience, in the zirconia sensor 100, the terminal to which the resistor 112 is connected is referred to as a high potential side terminal, and the terminal to which the voltage source 111 is connected is referred to as a low potential side terminal.

The resistor 110 and the switch 191 connected in series are connected between the high potential side terminal and the low potential side terminal of the zirconia sensor 100. The voltmeter 131 is connected between the high potential side terminal and the low potential side terminal of the zirconia sensor 100. The sink side terminal of the constant-current circuit 120 is connected to the high potential side terminal of the zirconia sensor 100 through the switch 192. The source side terminal of the constant-current circuit 120 is grounded. One end of the switch 193 is connected to the low potential side terminal of the zirconia sensor 100, and the other end is grounded.

By closing (turning on) the switch 191, the resistor 110 can be connected in parallel to the zirconia sensor 100. By turning on the switches 192 and 193, the constant-current circuit 120 can be connected in parallel to the zirconia sensor 100.

One end of the constant-current circuit 120 is grounded and the low potential side terminal of the voltage source 111 is grounded through the switch 193, which can constitute the constant-current circuit 120, enabling simplification of control over the constant-current circuit 120. The constant-current circuit 120 can also be grounded in common with the voltmeter 131 of the voltage measurement section 130. In a case where the low potential side terminal of the zirconia sensor 100 is grounded in the interior of the voltage measurement section 130, the switch 193 can be omitted.

Figure 3B:
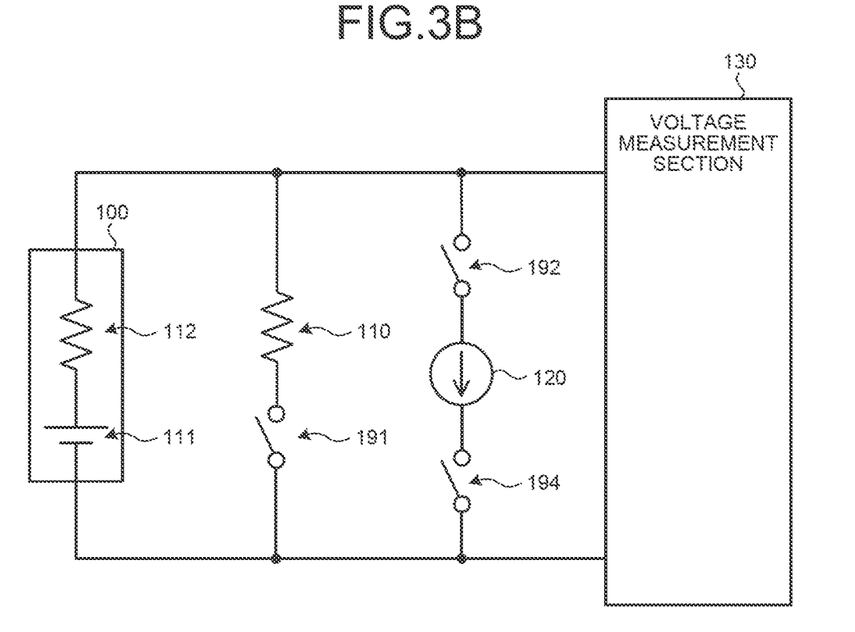
FIG. 3B is a diagram illustrating another example of measuring the resistance of the zirconia sensor according to the embodiment.

FIG. 3B is a diagram illustrating another example of measuring the resistance of the zirconia sensor according to the embodiment. FIG. 3B illustrates an example in which the source side terminal of the constant-current circuit 120 is connected to the low potential side terminal of the zirconia sensor 100 through a switch 194. Adopting a configuration to connect both ends of the constant-current circuit 120 to the zirconia sensor 100 with the switches 192 and 194 can reduce an impact of the constant-current circuit 120 after its connection to the zirconia sensor 100 is terminated.

An electric current can be passed through the constant-current circuit 120 in the reverse direction to FIG. 3B with respect to the zirconia sensor 100. The direction of the electric current passing through the constant-current circuit 120 can also be switched every time the resistance is measured.

Procedure for Measuring Resistance of Zirconia Sensor

Figure 4:
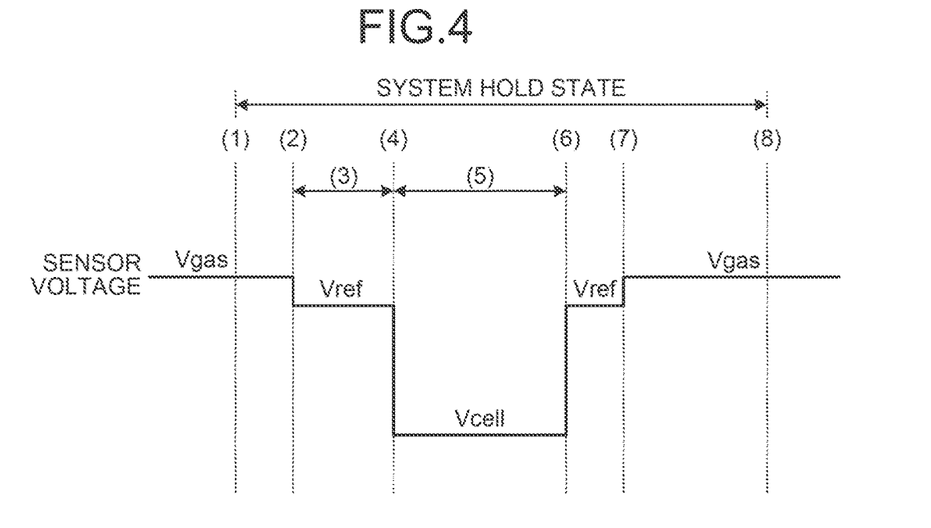
FIG. 4 is a diagram illustrating an example of a change in voltage of the zirconia sensor according to the embodiment.

FIG. 4 is a diagram illustrating an example of a change in voltage of the zirconia sensor according to the embodiment. FIG. 4 is a diagram illustrating a change in voltage of the zirconia sensor 100 when the resistor 112 of the zirconia sensor 100 is measured. The "sensor voltage" in FIG. 4 indicates the voltage of the zirconia sensor 100 measured by the voltmeter 131. Initially, the oxygen concentration meter 10 is in a state of detecting an oxygen concentration, and the zirconia sensor 100 outputs a voltage Vgas in accordance with the oxygen concentration of the gas introduced to the zirconia sensor 100. In the initial state, the switches 191 to 193 are off. The resistance value of the resistor 110 is referred to as Rref.

At (1), the oxygen concentration meter 10 is shifted to a system hold state. This shift stops outputting measurement results of oxygen concentrations to a host control system.

At (2), the switch 191 is turned on. The resistor 110 is connected in parallel to the zirconia sensor 100. As a result of this, the output voltage of the zirconia sensor 100 is level-shifted. The output voltage of the zirconia sensor 100 at this time is referred to as Vref. This Vref is measured by the voltmeter 131 at (3).

At (4), the switches 192 and 193 are turned on. The constant-current circuit 120 is connected in parallel to the zirconia sensor 100 and the resistor 110. Herein, the electric current that the constant-current circuit 120 supplies is referred to as Iref. The output voltage of the zirconia sensor 100 is further level-shifted by Iref. The voltage at this time is referred to as Vcell. This Vcell is measured by the voltmeter 131 at (5).

At (6), the switches 192 and 193 are turned off. The supply of the electric current from the constant-current circuit 120 is stopped.

At (7), the switch 191 is turned off. The connection of the resistor 110 is terminated. The output voltage of the zirconia sensor 100 returns to Vgas. The time elapsed between when the output voltage of the zirconia sensor 100 is changed (transitioned) from Vcell and when the output voltage of the zirconia sensor 100 returns to Vgas is referred to as transition time.

At (3), the system hold state is cleared.

The resistance value (Rcell) of the resistor 112 of the zirconia sensor 100 is represented by the following expression using Vref, Vcell, Iref, and Rref.

$$Rcell = \frac{(Vref - Vcell)l \times Rref}{Rref \times Iref - (Vref - Vcell)l} \quad (1)$$

Figure 5:
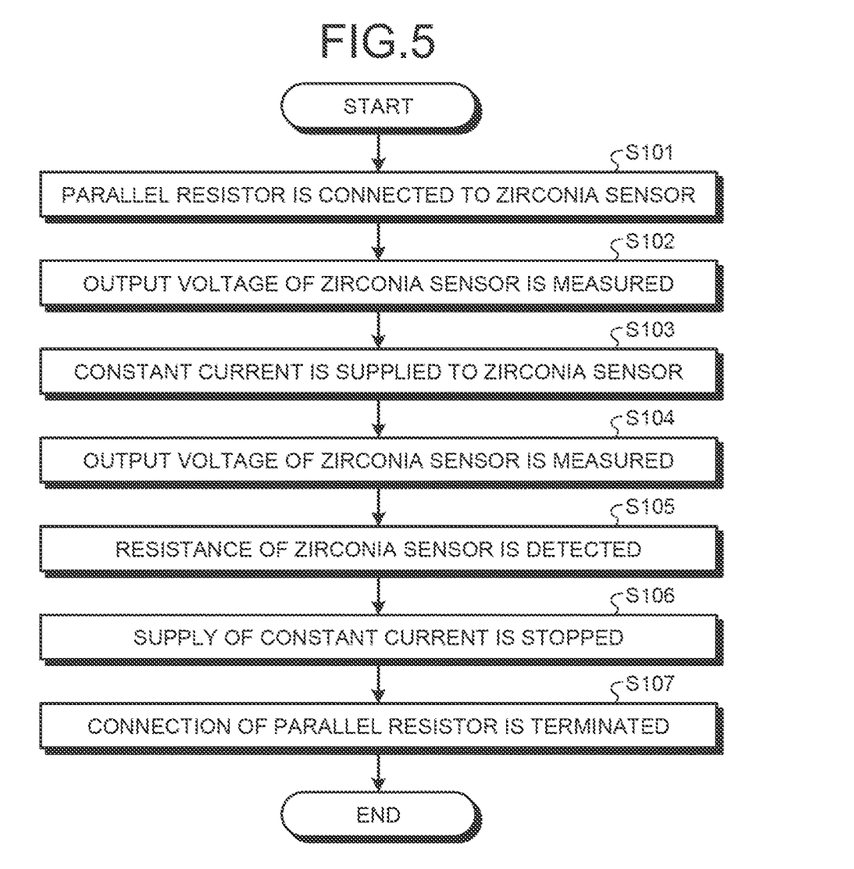
FIG. 5 is a diagram illustrating an example of a procedure for measuring the resistance of the zirconia sensor according to the embodiment.

FIG. 5 is a diagram illustrating an example of procedure for detecting the resistance of the zirconia sensor according to the embodiment. First, a parallel resistor is connected to the zirconia sensor 100 (step S101). This can be done by connecting the resistor 110 in parallel to the zirconia sensor 100. Next, the output voltage (Vref) of the zirconia sensor 100 is measured (step S102). Next, a constant current is supplied to the zirconia sensor 100 (step S103). This can be done by connecting the constant-current circuit 120 to the zirconia sensor 100. Next, the output voltage (Vcell) of the zirconia sensor 100 is measured (step S104).

Next, the resistance of the zirconia sensor 100 is detected based on Vref and Vcell (step S105). This can be done by using the above-mentioned expression (1) to calculate the resistance value (Rcell). Next, the supply of the constant current is stopped (step S106). This can be done by terminating the connection of the constant-current circuit 120. Next, the connection of the parallel resistor is terminated (step S107). This can be done by terminating the connection of the resistor 110. The resistance of the zirconia sensor 100 can be detected by following the procedure described above.

In this manner, the resistor 112 of the zirconia sensor 100 can be measured without using a standard gas or the like, which can increase convenience. Additionally, connecting the resistor 110 in parallel to the zirconia sensor 100 can further increase convenience. The effects of the resistor 110 are described.

Effect 1 of Parallel Resistor

In a circuit obtained by removing the resistor 110 and the switch 191 from the circuit of FIG. 3, the resistor 112 of the zirconia sensor 100 can also be detected. In this case, the resistor 112 can be calculated by the following expression.

Rcell=(Vgas−Vcell)/Iref

Herein, when the value of the resistance of the zirconia sensor 100 is relatively low, for example, 100Ω, letting Iref be 0.5 mA, the value of Vgas-Vcell can be about 50 mV. This voltage is substantially the same as the output voltage of the zirconia sensor 100 when the oxygen concentration is measured, and falls within the range of voltage that can be easily measured by the voltmeter 131.

Thereafter, if the resistance of the zirconia sensor 100 rises to 5 kΩ due to aging, the value of Vgas-Vcell rises to 2.5 V. In order to measure the voltage, range switching of the voltmeter 131, for example, is needed, which problematically makes the configuration of the voltmeter 131 complicated.

Contrarily, connecting the resistor 110 the value of which is about 100Ω in parallel enables Vgas-Vcell to be a few hundred mV even when the resistor 112 of the zirconia sensor 100 rises to a few kW. Thus, measurement of the voltage by the voltmeter 131 can be simplified.

Effect 2 of Parallel Resistor

Connecting the resistor 110 can also shorten return time after the resistance of the zirconia sensor 100 is measured. This is described by using an alternating-current equivalent circuit of the zirconia sensor 100.

Equivalent Circuit of Zirconia Sensor

Figure 6:
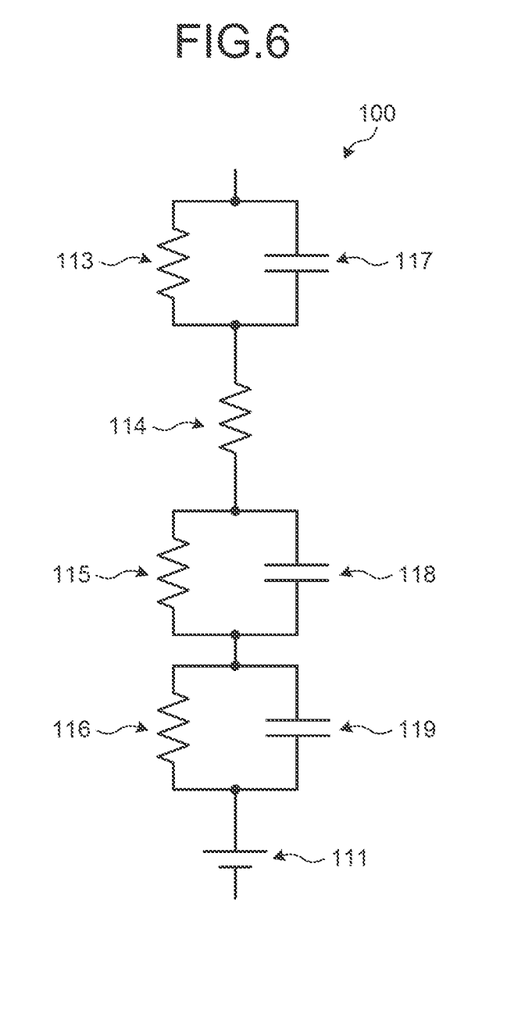
FIG. 6 is a diagram illustrating an example of an equivalent circuit of the zirconia sensor according to the embodiment.

FIG. 6 is a diagram illustrating an example of an equivalent circuit of the zirconia sensor according to the embodiment. FIG. 6 is a diagram illustrating an equivalent circuit of the zirconia sensor 100 to which a capacity is added. As illustrated in FIG. 6, the zirconia sensor 100 is made up of the voltage source 111, resistors 113 to 116, and capacitors 117 to 119. The zirconia sensor 100 in FIG. 6 is configured by connecting in series the resistor 113 and the capacitor 117 connected in parallel, the resistor 114, the resistor 115 and the capacitor 118 connected in parallel, the resistor 116 and the capacitor 119 connected in parallel, and the voltage source 111. FIG. 6 illustrates an alternating-current equivalent circuit of the zirconia sensor 100. Contrarily, the zirconia sensor 100 in FIG. 3 represents a direct-current equivalent circuit.

The resistors 113 and 116 represent electrode interface resistors. The resistor 114 represents a particle resistor. The resistor 115 represents a grain boundary resistor. These resistors 113 to 116 constitute the resistor 112 in FIG. 3. The resistors 113, 115, and 116 have capacitor components (the capacitors 117 to 119), respectively. These capacitor components serve as relatively large capacitance. The capacitors increase the transition time described in FIG. 4.

Change in Voltage of Zirconia Sensor

Figure 7A:
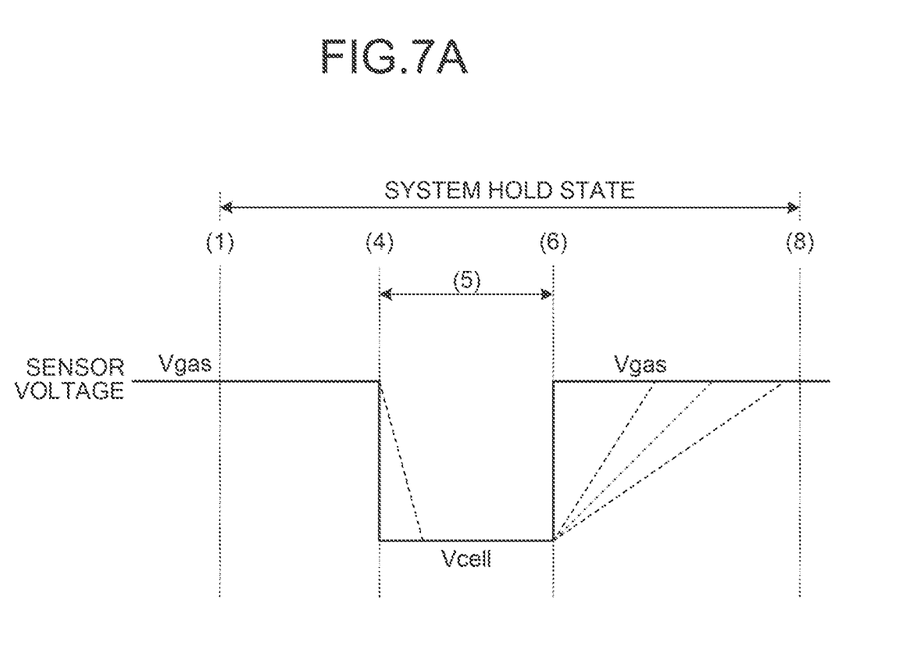
FIG. 7A is a diagram illustrating an example of a change in voltage of the zirconia sensor according to the embodiment.

FIG. 7A is a diagram illustrating an example of a change in voltage of the zirconia sensor according to the embodiment. FIG. 7A is a diagram illustrating, as a comparison example, a change in output voltage of the zirconia sensor 100 without the parallel resistor (resistor 110). The solid line in FIG. 7A indicates a change in voltage when the capacitor components are not added to the zirconia sensor 100. The dotted lines indicate a change in voltage when the capacitor components are considered.

Without the parallel resistor, a delay develops in the voltage transition at (4). However, the capacitor components are charged rapidly by the constant-current circuit 120, which results in a relatively short delay time. Meanwhile, at (6), a delay also develops when the connection of the constant-current circuit 120 is terminated. The delay is as a consequence of the discharge time of the capacitor components. Electricity is discharged from the capacitor components through the resistor 113 or the like connected in parallel, which results in a relatively long delay time. Thus, the time of the system hold state needs to be extended by delaying the timing for clearing the system hold state, for example.

Figure 7B:
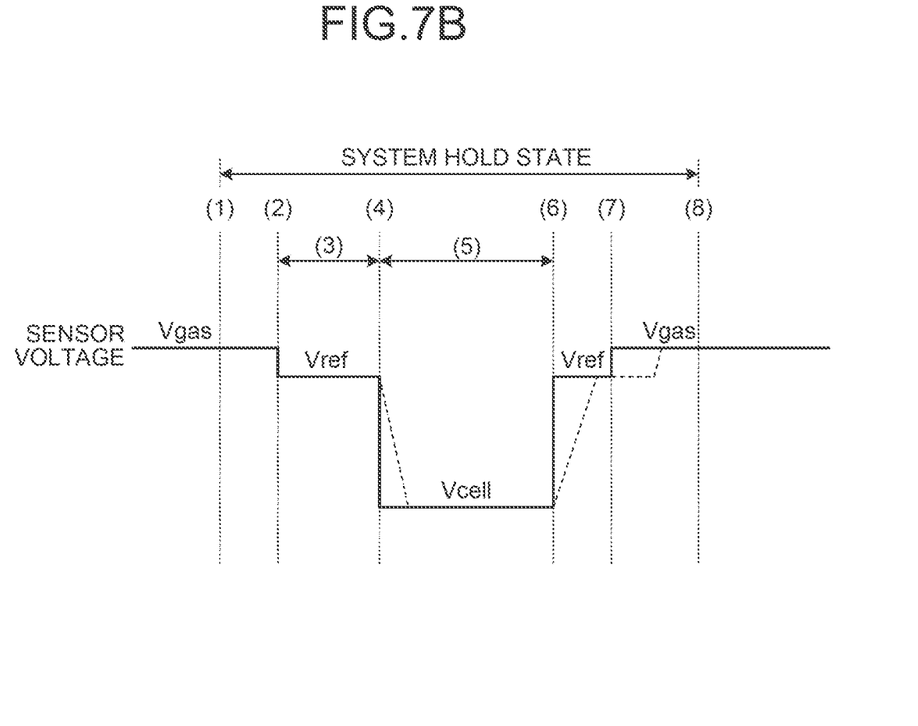
FIG. 7B is a diagram illustrating another example of a change in voltage of the zirconia sensor according to the embodiment.

FIG. 7B is a diagram illustrating another example of a change in voltage of the zirconia sensor according to the embodiment. FIG. 7B is a diagram illustrating a change in output voltage of the zirconia sensor 100 with the parallel resistor (resistor 110). In this case, at (6), the resistor 110 contributes to the capacitor components discharging, thereby shortening the discharge time, which can shorten the time of the system hold state. In this manner, connecting the resistor 110 in parallel to the zirconia sensor 100, can shorten the time of the system hold state. Consequently, the time for stopping the system to measure the resistance of the zirconia sensor 100 can be shortened.

Such a resistor 110 preferably has a resistance value of twice to ten times as many as the resistance value of the zirconia sensor 100 before aging. This can facilitate the voltmeter 131 measuring the resistance of the zirconia sensor 100. The resistor 110 further preferably has a resistance value of four to five times as many as the resistance value of the zirconia sensor 100 before aging. This can further shorten the discharge time of the capacitor components in the zirconia sensor 100.

Detection of Deterioration of Zirconia Sensor

Figure 8:
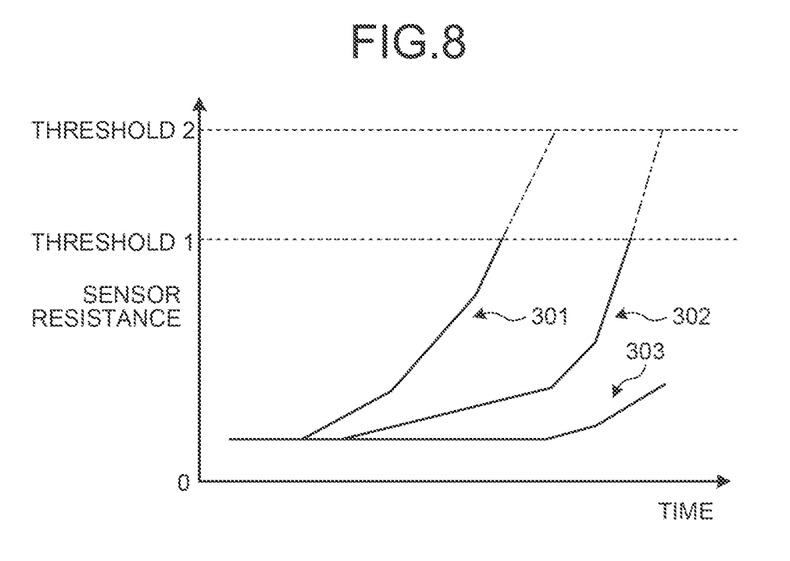
FIG. 8 is a diagram illustrating an example of detecting deterioration of the zirconia sensor according to the embodiment.

FIG. 8 is a diagram illustrating an example of detecting deterioration of the zirconia sensor according to the embodiment. FIG. 8 is a diagram illustrating changes in resistance of the zirconia sensor 100. The horizontal axis of FIG. 8 indicates the amount of time elapsed. The vertical axis indicates the resistance of the zirconia sensor 100. A threshold 2 indicates the resistance value for detecting deterioration of the zirconia sensor 100. The zirconia sensor 100 the resistance value of which has reached the threshold 2 can be determined to be no longer usable for measuring the oxygen concentration because of deterioration. A threshold 1 is the resistance value for conducting a predictive diagnosis that predicts the time that elapses before the zirconia sensor 100 deteriorates. The zirconia sensor 100 the resistance value of which has reached the threshold 1 can be subject to the predictive diagnosis. The predictive diagnosis can be conducted by the deterioration detection section 20 described in FIG. 1.

Graphs 301 to 303 in FIG. 8 chart changes in resistance of the zirconia sensor 100 that differ from each other. These graphs have different forms depending on the usage state, for example. The predictive diagnosis can be conducted on the zirconia sensor 100 shown in the graphs 301 and 302 in which the resistance value has reached the threshold 1. The graphs indicated by dash-dotted lines in FIG. 8 chart results of the predictive diagnosis. The predictive diagnosis can be conducted by using the resistance value held in the holding section 30 described in FIG. 1. For example, the deterioration detection section 20 can conduct the predictive diagnosis by extending the graph 301 or the like in FIG. 8. The predictive diagnosis can be conducted also by calculating an approximate curve by means of regression analysis, for example. The results of the predictive diagnosis are conveyed to a user or the like through the conveying section 40.

In addition to the predictive diagnosis, the deterioration detection section 20 can also conduct machine learning using big data made up of data on oxygen concentrations of the zirconia sensor 100 and environmental data on ambient temperature, humidity, and the like, and conduct an AI diagnosis. Thus, an analysis of can be performed of predictions about the life of the zirconia sensor 100 depending on use conditions, for example.

The deterioration detection section 20 and the holding section 30 can be implemented as software applications for computers and servers.

In this manner, the resistance of the zirconia sensor 100 is measured by connecting the constant-current circuit 120 to the zirconia sensor 100, so that a standard gas or the like can be omitted, which can increase convenience. The resistance of the zirconia sensor 100 can be measured easily, which can increase population parameters for resistance measurement data, enabling an analysis of predictions about the life of the zirconia sensor 100, for example.

When the resistance of the zirconia sensor 100 is measured, connecting the resistor 110 in parallel can narrow the measurement range of the output voltage and also shorten return time to its steady state. This can further increase convenience.

The effects described herein are illustrated by example and are not limited. Other effects may be possible.

The procedure described in the above-mentioned embodiment may be interpreted as a method including a series of the procedural steps, or may be interpreted as a computer program that causes a computer to perform the procedural steps or as a recording medium that stores therein the computer program. As the recording medium, a compact disc (CD), a MiniDisc (MD), a digital versatile disc (DVD), a memory card, and a Blu-ray (registered trademark) disc, for example, can be used.

What is claimed is:

1. An oxygen concentration meter comprising:
a zirconia sensor;
a resistor that is connected in parallel to the zirconia sensor in detection of a resistance of the zirconia sensor;
a constant-current circuit that is connected in parallel to the zirconia sensor and the resistor in detection of the resistance of the zirconia sensor, and that supplies an electric current;
a resistance detection section configured to detect the resistance of the zirconia sensor, based on a voltage of the zirconia sensor in accordance with the supplied electric current, for detecting deterioration in the zirconia sensor; and
an oxygen concentration detection section configured to detect an oxygen concentration of gas to be measured that is supplied to the zirconia sensor in which the resistor and the constant-current circuit are not connected, based on the voltage of the zirconia sensor resulting from an oxygen concentration difference between the gas to be measured and a reference gas.

2. The oxygen concentration meter according to claim 1, wherein the resistance detection section detects the resistance of the zirconia sensor, based on the voltage of the zirconia sensor when the resistor is connected and the voltage of the zirconia sensor when the constant-current circuit is further connected and an electric current is supplied.

3. The oxygen concentration meter according to claim 1, further comprising a voltage measurement section configured to measure the voltage of the zirconia sensor, wherein
the resistance detection section detects the resistance, based on the measured voltage of the zirconia sensor, and
the oxygen concentration detection section detects the oxygen concentration, based on the measured voltage of the zirconia sensor.

4. The oxygen concentration meter according to claim 3, wherein the constant-current circuit is grounded in common with the voltage measurement section.

5. An oxygen concentration detection system comprising:
a zirconia sensor;
a resistor that is connected in parallel to the zirconia sensor in detection of a resistance of the zirconia sensor;

a constant-current circuit that is connected in parallel to the zirconia sensor and the resistor in detection of the resistance of the zirconia sensor, and that supplies an electric current;

a resistance detection section configured to detect a resistance of the zirconia sensor, based on a voltage of the zirconia sensor in accordance with the supplied electric current, for detecting deterioration in the zirconia sensor;

an oxygen concentration detection section configured to detect an oxygen concentration of gas to be measured that is supplied to the zirconia sensor in which the resistor and the constant-current circuit are not connected, based on the voltage of the zirconia sensor resulting from an oxygen concentration difference between the gas to be measured and a reference gas; and a deterioration detection section configured to detect an abnormality in the zirconia sensor, based on the detected resistance of the zirconia sensor.

6. An oxygen concentration detection system comprising:
a zirconia sensor;
a resistor connected in parallel to the zirconia sensor;
a constant-current circuit that is connected in parallel to the zirconia sensor and the resistor, and that supplies an electric current;
a resistance detection section configured to detect a resistance of the zirconia sensor, based on a voltage of the zirconia sensor in accordance with the supplied electric current;

an oxygen concentration detection section configured to detect an oxygen concentration of gas to be measured that is supplied to the zirconia sensor, based on the voltage of the zirconia sensor resulting from an oxygen concentration difference between the gas to be measured and a reference gas;

a deterioration detection section configured to detect an abnormality in the zirconia sensor, based on the detected resistance of the zirconia sensor; and a holding section configured to hold the detected resistance of the zirconia sensor, wherein the deterioration detection section further predicts deterioration of the zirconia sensor, based on the held resistance of the zirconia sensor.

7. The oxygen concentration detection system according to claim 6, further comprising a conveying section configured to convey the deterioration.

8. A method of detecting a resistance of a zirconia sensor that generates electromotive force according to an oxygen concentration difference between a gas to be measured and a reference gas, the method comprising detecting a resistance of a zirconia sensor, based on a voltage of the zirconia sensor when a resistor is connected in parallel to the zirconia sensor and a voltage of the zirconia sensor when a constant-current circuit is connected in parallel to the zirconia sensor and the resistor and an electric current is supplied.

* * * * *